United States Patent [19]

Shukla

[11] Patent Number: 5,733,442
[45] Date of Patent: *Mar. 31, 1998

[54] MICRODIALYSIS/ MICROELECTRODIALYSIS SYSTEM

[76] Inventor: Ashok K. Shukla, 10024 Century Dr., Ellicott City, Md. 21042

[*] Notice: The term of this patent shall not extend beyond the expiration date of Pat. No. 5,340,449.

[21] Appl. No.: 225,667

[22] Filed: Apr. 11, 1994

Related U.S. Application Data

[63] Continuation-in-part of Ser. No. 623,875, Dec. 7, 1990, abandoned, and Ser. No. 965,862, Oct. 23, 1992, Pat. No. 5,340,449.
[51] Int. Cl.⁶ .................................................. B01D 63/00
[52] U.S. Cl. .................. 210/94; 210/195.2; 210/223; 210/243; 210/321.67; 210/321.68; 210/323.1; 210/500.21; 204/627
[58] Field of Search ................. 210/644, 34.67, 210/321.68, 94, 323.1, 222, 223, 195.2, 500.21, 242; 704/627

[56] References Cited

U.S. PATENT DOCUMENTS

| | | | |
|---|---|---|---|
| 3,503,877 | 3/1970 | Berry | 210/321.67 X |
| 3,623,611 | 11/1971 | Reiley et al. | |
| 3,749,646 | 7/1973 | Pirt | 210/644 X |
| 4,450,076 | 5/1984 | Medicus et al. | |
| 4,960,521 | 10/1990 | Keller | 210/321.68 X |
| 5,183,564 | 2/1993 | Hong | |

*Primary Examiner*—David A. Reifsnyder

[57] ABSTRACT

A microdialysis system for the dialysis of small sample volumes of protein, nucleic acid, peptide, and other biomolecules has been developed. The device may contain a built-in magnet to permit remote rotation of the device during dialysis. Double sided dialysis chambers can be used for electrodialysis, electroelution, or electroconcentration. Two or more chambers can be joined either by a union or directly for equilibrium dialysis, or other applications.

13 Claims, 7 Drawing Sheets

MICRODIALYSIS/ MICROELECTRODIALYSIS SYSTEM

RELATED APPLICATION

This application is a continuation-in-part of U.S. application, Ser. No. 07/623,875, filed Dec. 7, 1990 (now abandoned), and U.S. application, Ser. No. 07/965,862, filed Oct. 23, 1992, now U.S. Pat. No. 5,340,449

BACKGROUND OF THE INVENTION

This invention relates to a device and method for the dialysis and concentration of macromolecules (including proteins and nucleic acids) in small sample volumes. A number of methods are currently available or published:

1. Floating membrane dialysis: A membrane is floated on water or buffer and a small droplet is placed on the membrane for dialysis. In this method, the volume of the sample can be changed by evaporation and it is difficult to handle the sample after dialysis or even an overflow of the sample can mix it with the buffer.

2. A device to handle multiple samples is developed by Pierce, Inc., which as a capability of micro-dialysis but the exchange buffer volume is limited and it is an open system, which allows a cross-flow of the sample from one well to another.

3. Hong described in U.S. Pat. No. 5,183,564, the dialysis of samples by shaking the sample compartment. The dialysis chambers are fused with the membrane, however, giving the user no choice of different membranes. The system is an open system and an increase in the volume is possible. The volume of the dialysate chamber is fixed therefore, in some cases a frequent exchange of buffers in the dialysis chamber is required.

The principle objective of the invention is to provide a simple, efficient method for the dialysis of biological samples specially in small volumes in microliter range. This invention gives flexibility in selecting the volume of the samples as well as the pore size and type of the membrane. Further, the same unit can be used for the concentration of the sample without transferring the sample from one system to another.

Another advantage is that of using inert material, for example, TEFLON™, which does not bind most of the biomolecules as compared to other plastic materials. TEFLON™ dialysis chambers are autoclaveable and easy to clean.

Another advantage is each chamber be separately dialyzed as compared to multi-chamber of shaking dialysis system as described above, the small molecule can contaminate the other sample by back dialysis from buffer to the dialysis chamber.

Another advantage is that dialysis and concentration can be done in the same chamber, so there is no loss of sample during the transfer from one container to the other. The sample is concentrated on a TEFLON™ surface so there is high recovery, as compared to the centrifugal method, where the sample concentrates on the membrane and it is known that membranes may bind many proteins and biomolecules. Further, centrifugal force may cause the biomolecules to pass through the membrane, reducing recovery.

Another advantage is that these dialysis chambers can be used for electroelution, electrodialysis, electroconcentration, on-line dialysis, on-line electrodialysis, on-line electroconcentration.

Another advantage is that these chambers can be joined together either by a union or directly with male-female connector. By using two or more chambers, a very selective filtration can be achieved by using membranes of different molecular weight cut-off between two chambers.

Another advantage of this dialysis chamber is that it can be immersed in any buffer and it is leakproof. Therefore, without any extra unit this can be immersed in a bath of any suitable temperature for temperature controlled dialysis. This is not possible in other commercially available units.

The advantage of a serpentine dialyser is that it can run at a very small flow rate of 1–1000 ml/min. The flow rate of the sample and type of membrane can determine the percentage of desalting. The total volume of the serpentine dialyser can be controlled by using the different length and depth of the serpentine. In combination with liquid chromatography, this serpentine dialyser is a very useful tool. However, without serpentine dialyser, sample should be collected in fractions and dialyzed in dialysis chambers individually.

BRIEF DESCRIPTION OF THE DRAWINGS

The various features of novelty which characterize the invention are pointed out with particularity in the claims annexed to and forming a part of this disclosure. For a better understanding of the invention, its advantages and objects, reference is made to the accompanying drawings and descriptive matter in which a preferred embodiment of the invention is illustrated.

DETAILED DESCRIPTION OF THE INVENTION AND PREFERRED EMBODIMENT

Figure 1:
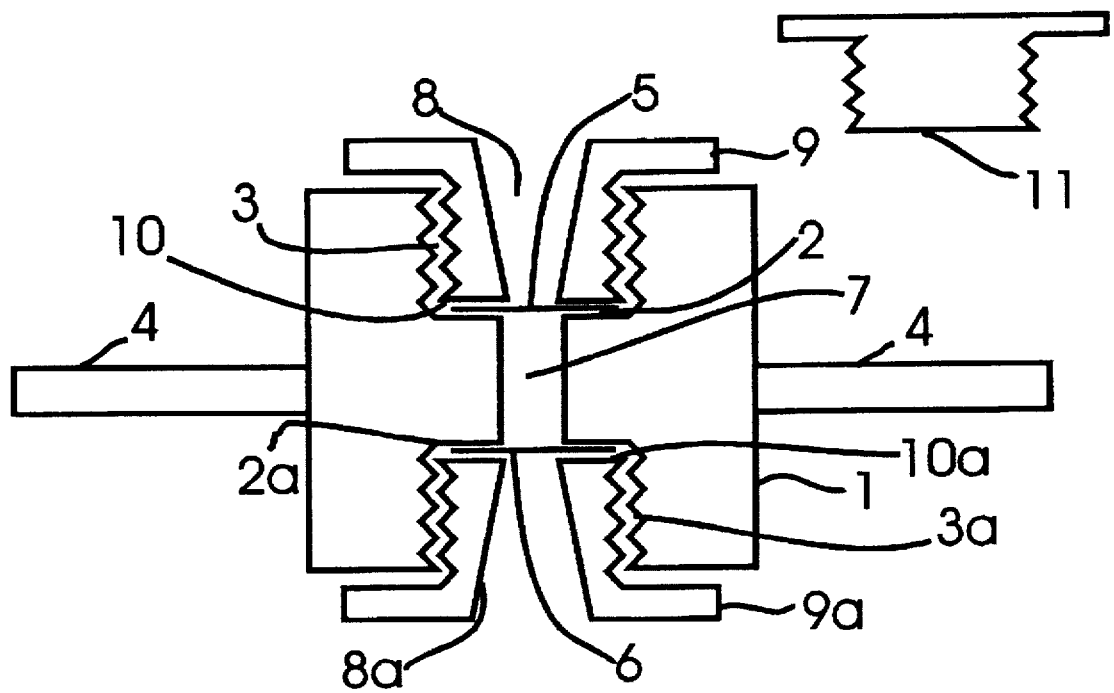
FIG. 1 shows an expanded view of a dialysis chamber according to the present invention.

The electroelution chambers described in the co-pending application can also be used for the dialysis and/or concentration of samples. The dialysis of small sample volumes (10–5000 μl or larger) can be achieved by this method. The advantage of this method over the prior art is that it is very simple, easy to use and requires no gaskets.

In this invention a dialysis chamber has been described for the dialysis of small sample volumes (in μl to ml range). Furthermore, same device can be used for the concentration of the sample. The dialysis chamber is made of any suitable plastic material, including but not limited to plastic or glass. Suitable plastics include TEFLON™, acrylics and the like. The outer surface of dialysis chamber can be conical, round or any other shape is made of TEFLON™, glass or other plastic materials which do not react with the solutions used for the dialysis or buffer. For example, the chamber can be cylindrical for the use with a round gasket 4 to prevent leakage. Further, the chamber can have a cubical or rectangular shape to prevent it from rotating or rolling away from a specific position within a tank or other containers.

The dialysis chamber 1 has a through-hole 7, which can be of different shape, sizes and diameters. This hole determines the volume of the dialysis sample. On both sides of the hole 7, there are bigger holes (wells) 3 and 3a, which are tapered and may be sealed by seals (5 and 6).

In the case of dialysis, the wells are sealed by membrane 5 and 6, which can be of the same or of different types, such as different materials or different molecular size exclusions, described below. These membranes can be of different materials, for example, cellulose acetate, nitrocellulose, PVDF, or TEFLON™. The membranes are semipermeable so as to trap macromolecules while allowing small molecules to pass through depending on the molecular weight cutoff of these membranes. Membranes 5, 6 can be placed at platform 2 and 2a, respectively, via a tapered screw 9, 9a. The screws 9 and 9a and the chamber can be joined, for example, by a threaded fitting (as in FIG. 1) or by a tapered quickfit or snap-type fitting. In addition, the chamber 1 can be provided with threads 12 on its exterior to cooperate with threads 13 on the screws 9, 9a as shown in FIG. 2. This configuration is advantageous as it positions the membranes 5, 6 in close contact with the liquid in the tank to allow faster interaction.

The device may also be used as a macromolecule crystal growth system by sealing one well with a suitable transparent window (6) from which crystal growth may be observed. Buffer solution is slowly flowed through inlet (20) and circulated through outlet (21), thereby causing macromolecules to precipitate due to changes in pH.

The screws 9, 9a are tapered to fit the holes 3 and 3a so that they can be screwed into the holes 3 and 3a, respectively.

Screws 9, 9a are made of the same or compatible material as the chamber 1. Screws 9, 9a have a smooth surface 10, 10a which fit on the membranes 5 or 5a and tighten on the surface 2, 2a in such a way that no fluid can leak from the hole 7. Leak-proof tightening can also be achieved by using o-ring. The membranes 5, 6 have the same diameter as the surface 10, 10a.

Screw 9 or 9a has a through-hole 8 or 8a, respectively. The hole 8 and 8a can be conical or cylindrical, and can be of a different size and shape.

Figure 2:
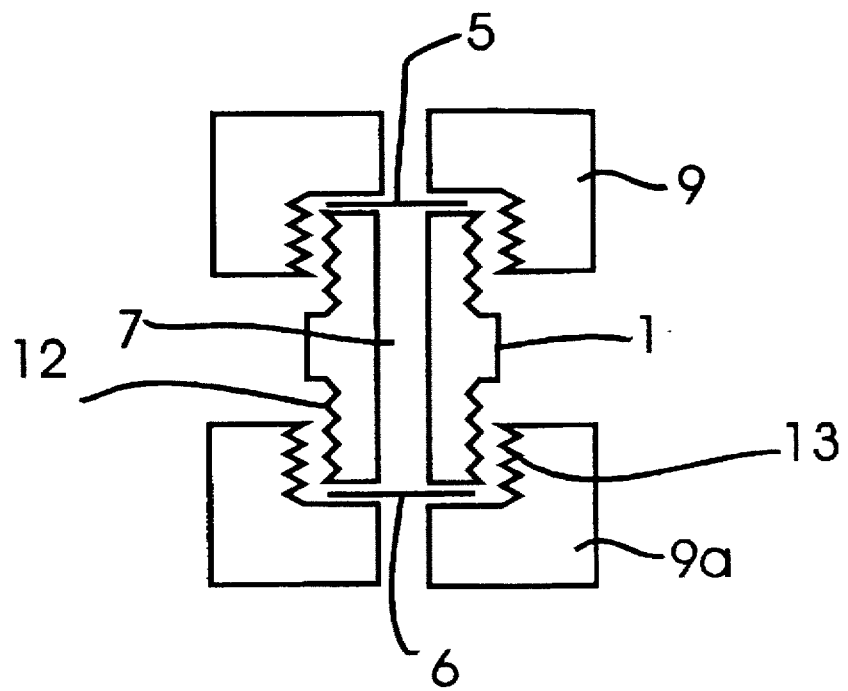
FIG. 2 shows the dialysis chamber having threads to cooperate with threaded screws in accordance with the present invention.

As shown in FIG. 1, if in the dialysis chamber, one of the screws (8 or 9a) is replaced by a screw without through hole (11), the dialysis chamber can be used for the concentration of the samples. Further, this configuration can be kept under vacuum for further concentration of the sample in the sample compartment (7). The advantage of this type of concentration over centrifugal concentration of the sample is that the sample is concentrated on the TEFLON™ surface as compared to the centrifugal method where the sample is concentrated on the membrane. This method yields a much higher recovery of the sample as the sample is not in contact with the membrane after replacement with the screw (11) and therefore cannot stick to the membrane.

Figure 3:
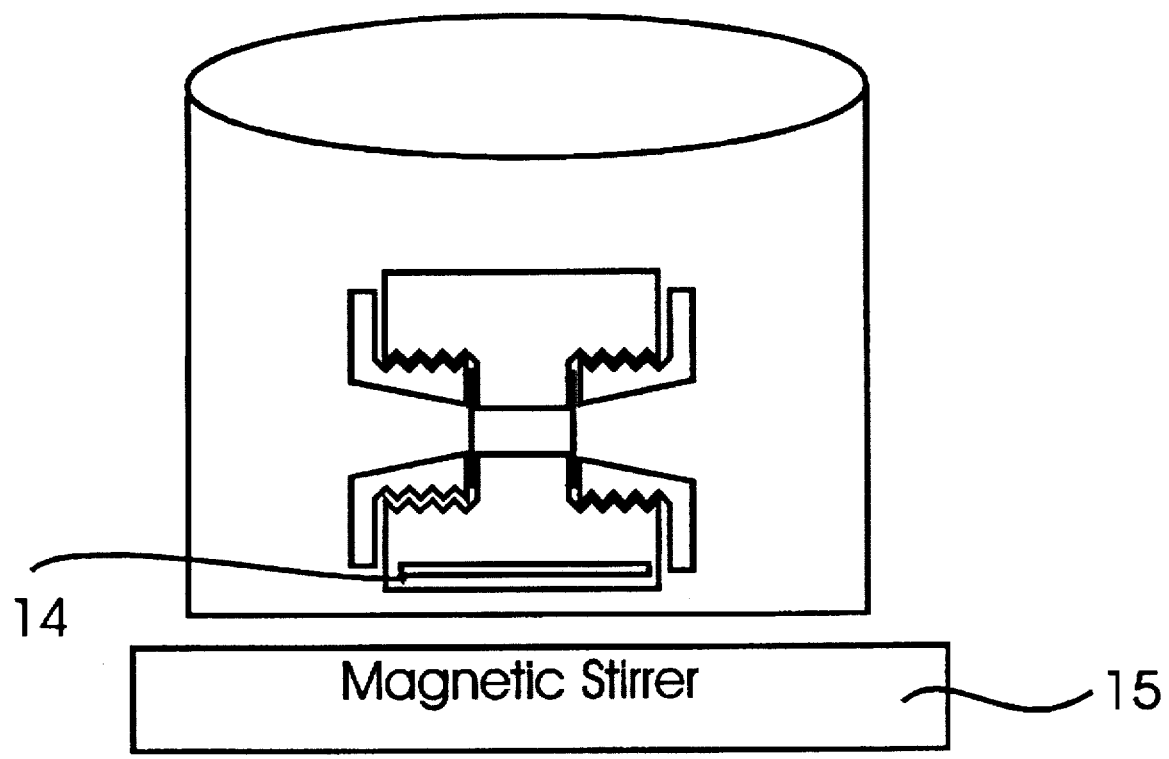
FIG. 3 shows a dialysis chamber having a magnet disposed therein in accordance with the present invention.

As shown in FIG. 3, a magnet 14 can be placed inside the chamber wall in such a way that it has no contact with the liquid. This allows use of a magnetic stirrer 15 for dialysis or exchange of buffer. The magnet arrangement depicted in FIG. 5 is advantageous because the centrifugal force created by the stirrer 15 and magnet 14 interaction accelerates the exchange of molecules at the membranes 5, 6.

Figure 4:
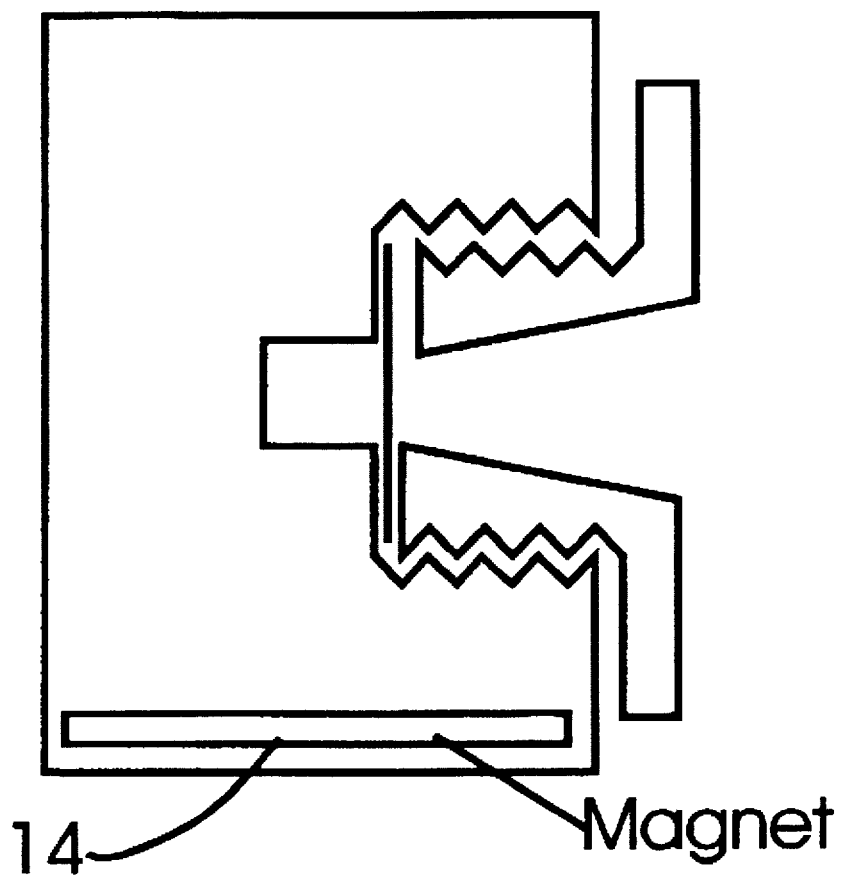
FIG. 4 shows a dialysis chamber with one sided hole and a built-in magnet.

With reference to FIG. 4, a single-sided chamber with built-in magnet can be used for simple dialysis as well as concentration of samples.

The chamber in FIG. 1 can be used for electrodialysis, by placing the dialysis chamber in any electrophoresis tank in such a way that the chamber separates the anode and cathode buffer and the current flows through hole 7.

Figure 5:
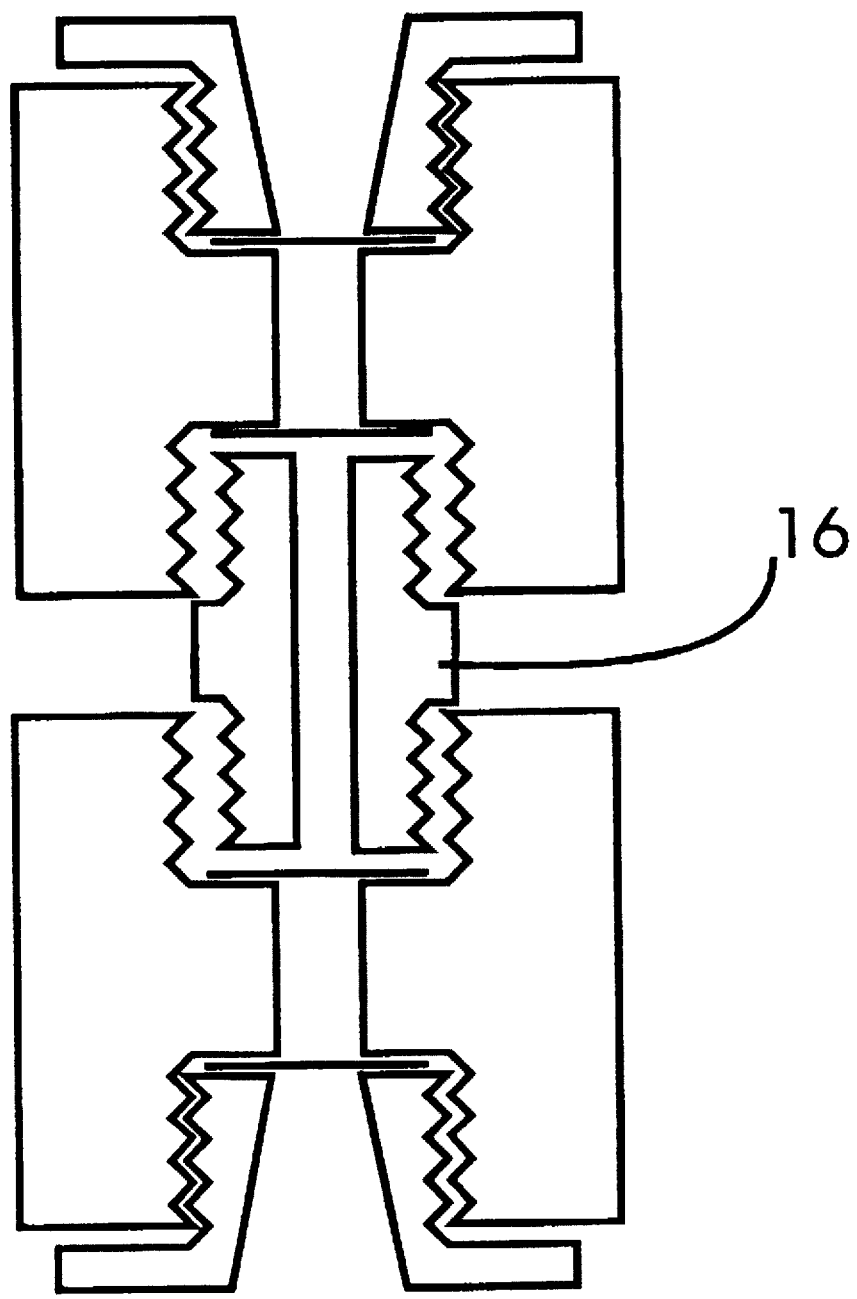
FIG. 5 shows the joining of two chambers by a union.
Figure 6A:
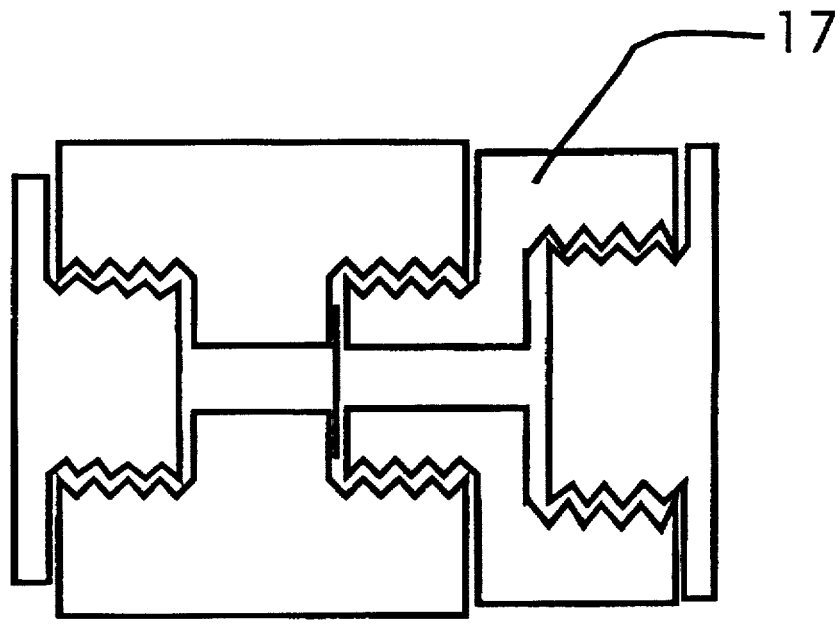
FIG. 6a shows the joining of two chambers without a union.
Figure 6B:
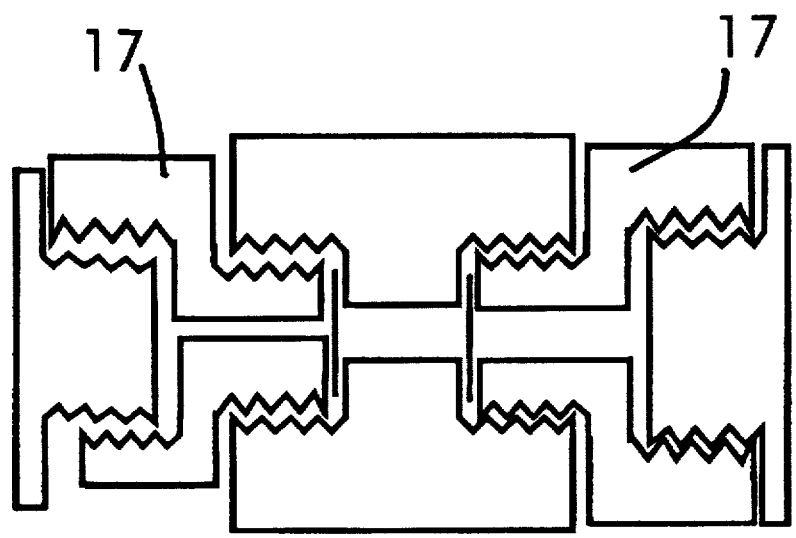
FIG. 6b shows the joining of multiple chambers without a union.
Figure 7A:
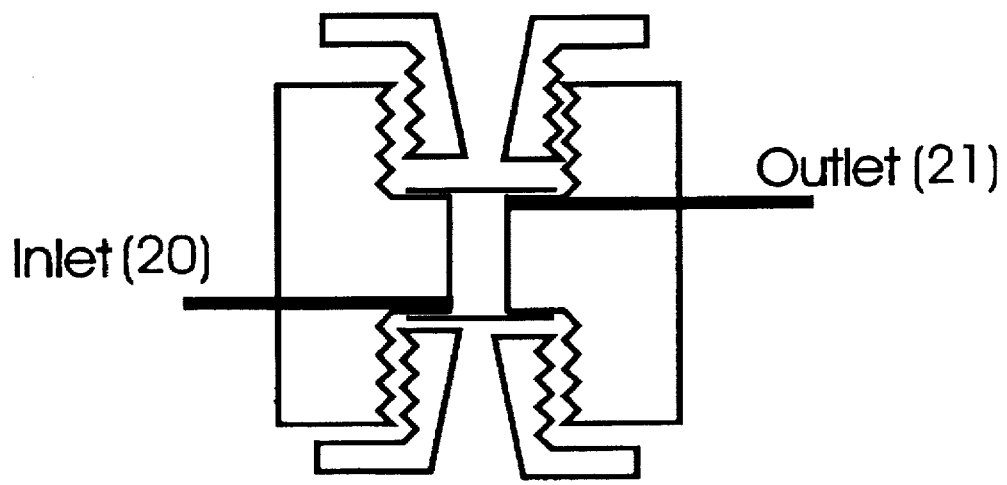
FIG. 7a and 7b shows an inlet and outlet in a dialysis chamber.
Figure 7B:
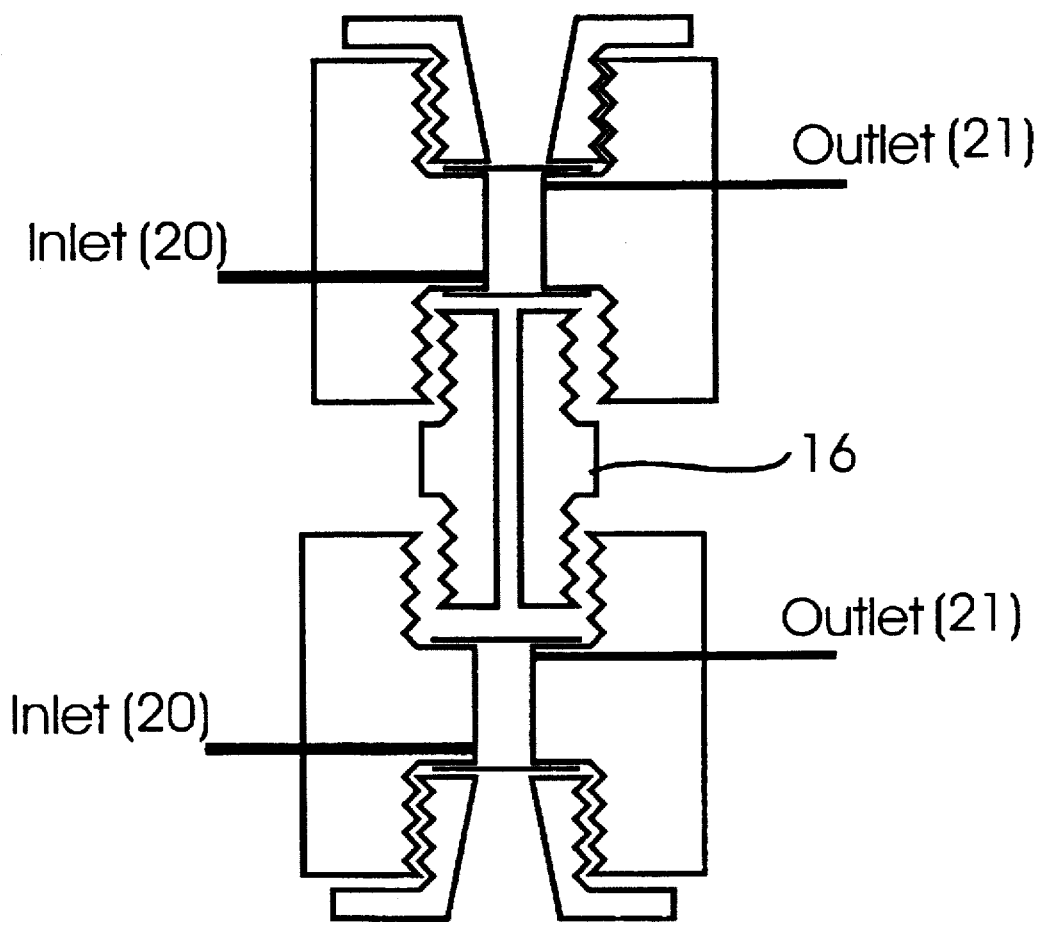

Two or more dialysis chambers can be joined either by a union 16 as in FIG. 5, or by the configuration as shown in FIG. 6a and 6b. By using the attachment 17, two chambers joined without the union have no dead volume. This two or more chamber configuration can be used for the electroconcentration of the samples. Further, using a throughflow chamber as in FIGS. 7a & 7b, the electrodialysis or electroconcentration of larger volumes can be achieved.

Figure 8:
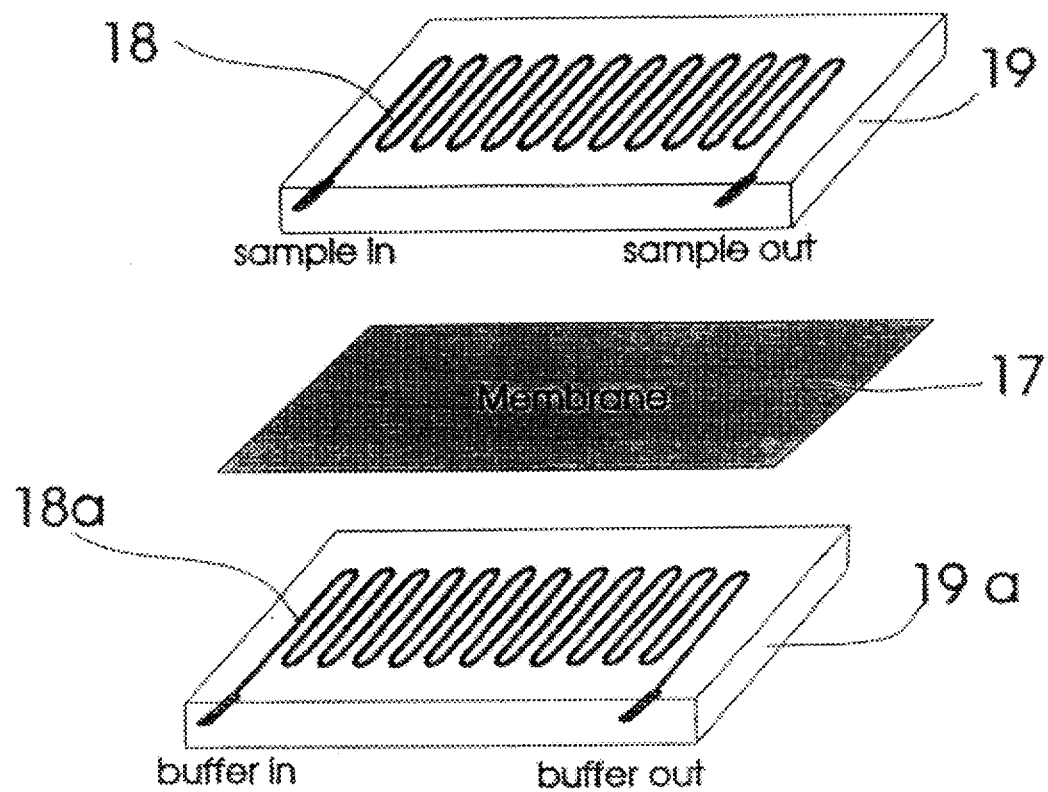
FIG. 8 shows a serpentine dialysis chamber.

FIG. 8 shows two chambers 19 and 19a, which contain serpentine channels (18 & 18a) as flow path for the samples. These can be superimposed and the volume of the serpentine 18 or 18a can be changed by changing the depth of the serpentine. However, the length of the serpentine is constant. These two serpentines are held together (separated by a membrane 20 between them) using a clamp. The sample flows in from one end and flows out from the other end in one of the serpentines. In the other serpentine separated by a membrane, a constant flow of the buffer is maintained using a pump. This serpentine dialyser can be used in combination with a liquid chromatography column for the desalting or concentration of small molecules, which can pass through the membrane.

EXAMPLES OF APPLICATIONS

1. DIALYSIS OF SALTS FROM PROTEINS

Take a 100 µl dialysis chamber (1). A membrane with a molecular weight cut off less than protein's molecular weight should be taken. First place membrane 6 and tighten with screw 9a and then fill the well 7 with the protein solution. Put another membrane of the same molecular weight cut-off on the other side and tighten with screw (9). Drop the dialysis chamber in a beaker with a desired buffer. If the dialysis chamber does not have a built-in magnet, a stirring bar and magnetic stirrer can be used to accelerate the dialysis process. However, if the dialysis chamber has a built-in magnet, it will further accelerate the dialysis. After the dialysis is complete, the sample can be concentrated by removal of the membrane of one side and the replacement of through hole screw (9 or 9a) with the solid screw (11). Place the chamber under vacuum. The water or solvent will diffuse through the membrane and the sample will be concentrated on the chamber bottom.

2. EQUILIBRIUM DIALYSIS

Two equilibrium dialysis chambers as shown in FIG. 6a are used for the study of equilibrium dialysis. The chambers can be opened at any time and a small sample aliquot can be taken for the determination of free biomolecules or drugs. Furthermore, three chambers can also be joined for the study of protein binding assays (FIG. 6b). The middle chamber is filled with the drug; the chamber on one side is filled with the protein and the chamber on the other side with the control buffer. A small aliquot is taken time to time to analyze the binding of biomolecule or drug to the protein. If the drug concentration is higher in the protein chamber than in the control chamber, it shows that the protein is binding the drug. This is a very simple and time saving method for the protein binding assay and it could be very useful in testing of new drugs.

3. ELECTRODIALYSIS

Charged molecules can be concentrated by electrodialysis. Chambers of different volume are used for the concentration of samples. A sample can be placed in a large volume chamber, the whole unit assembled as in FIG. 5 and placed in an electrophoretic tank. The buffers are chosen according to the application, using criteria known to those skilled in the art. A current is applied in such a direction that the biomolecule moves from the larger chamber to the smaller chamber according to the charge of the molecule. Within 5–10 min., most of the sample concentrates in the small chamber. By using a through flow chamber (FIG. 7a and 7b) a continuous concentration can be achieved. Before injecting the sample in High Performance Liquid Chromatography (HPLC), the sample can be concentrated, desalted, or partially filtered using appropriate membrane or using through flow cell chambers in combination with an HPLC injection valve.

4. ON-LINE DIALYSIS

A serpentine chamber can be used on-line with the HPLC for the removal of salts on-line. Serpentine chambers of different volume are available and the flow rate at each side can also be controlled. This facilitates the concentration of the dialysate for protein binding assays. The serpentine system is also useful for the removal of unbound radioactive label compound in affinity chromatography, and sample purification during the separation.

While a specific embodiment of the invention has been shown and described in detail to illustrate the application of the principles of the invention, it will be understood that the invention may be embodied otherwise without departing from such principle and that various modifications, alternate constructions, and equivalents will occur to those skilled in the art given the benefit of this disclosure. Thus, the invention is not limited to the specific embodiment described herein, but is defined by the appended claims.

What is claimed is:

1. A Microdialyser device comprising, a plurality of sample chambers; said chambers having one or more holes; said holes being a well, a cavity or a through-hole; said chambers being releasably sealable by one or more screw caps having a through hole; the device having a first membrane, for the passage of fluid and/or molecules, and a magnet.

2. A device as in claim 1, further comprising one or more membranes in addition to said first membrane, said one or more membrane being positioned respectively between the hole of one of said chambers and the corresponding cap.

3. A device as in claim 1 or 2, further comprising an inlet and outlet in the sample chamber through the chamber wall for the continuous flow of the fluid and or molecules through the sample chamber either for recirculation or from an outside sample reservoir.

4. A method of dialysis or concentration of molecules, comprising the steps of providing a microdialyser device as in claim 3 selecting membranes suitable for the desired electrodialysis and/or electroconcentration, placing the device in a desired buffer, and applying a suitable electric current.

5. A device as claimed in claim 3, comprising two or more union chambers in series; said union chambers joined either directly or through said sample chamber and having membranes of the same or different porosity placed in between them.

6. A method of dialysis or concentration of molecules, comprising the steps of providing a microdialyser device as in claim 5 selecting membranes suitable for the desired electrodialysis and/or electroconcentration, placing the device in a desired buffer, and applying a suitable electric current.

7. A device as in claim 3, wherein one of said plurality of sample chambers comprises one open end releasably sealable by a transparent window.

8. A method of dialysis or concentration of molecules, comprising, the steps of providing a microdialyser device as in claims 1 or 2, selecting membranes suitable for the desired electrodialysis and/or electroconcentration, placing the through-holed device in a desired buffer, and applying a suitable electric current.

9. A device as claimed in claim 1, further comprising a external magnet to impart a spinning motion to the device.

10. A device as in claim 1, wherein said one or more chambers are releasably sealable by one or more caps, each said chamber and one, but only one of the said caps having a through-hole for the passage of the fluid and or molecules.

11. A device as claimed in claim 1, comprising two or more union chambers in series; said union chambers joined either directly or through said sample chamber and having membranes of the same or different porosity placed in between them.

12. A method of dialysis or concentration of molecules, comprising the steps of providing a microdialyser device as an claim 11, selecting membranes suitable for the desired electrodialysis and/or electroconcentration, placing the device in a desired buffer, and applying a suitable electric current.

13. A microdialyser device comprising one sample chamber having a sample-well and the open end of the said sample-well being releasably sealable by a screw having a through hole for dialysis or exchange of buffer and a membrane placed between the open end of said well and the said cap; said sample chamber contains a magnet.

* * * * *